United States Patent [19]
Kyburz et al.

[11] 3,952,017
[45] Apr. 20, 1976

[54] TRICYCLIC COMPOUNDS
[75] Inventors: Emilio Kyburz, Reinach; Hans Spiegelberg, Basel, both of Switzerland
[73] Assignee: Hoffmann-La Roche Inc., Nutley, N.J.
[22] Filed: Aug. 30, 1974
[21] Appl. No.: 501,931

Related U.S. Application Data
[60] Division of Ser. No. 270,674, July 11, 1972, which is a continuation-in-part of Ser. No. 818,146, April 21, 1969; abandoned.

[30] Foreign Application Priority Data
May 3, 1968 Switzerland.......................... 6612/68

[52] U.S. Cl............................ 260/340.9; 260/471 A; 260/562 P; 260/566 R; 260/570.6; 260/570.8 TC; 260/570.9; 260/611 A; 260/649 R; 260/665 R; 260/668 F; 260/669 R; 424/330
[51] Int. Cl.².................... C07C 93/00; C07D 317/28
[58] Field of Search................. 260/340.9, 570.8 TC

[56] References Cited
UNITED STATES PATENTS
3,454,643  7/1969  Cope et al. ................. 260/570.8 TC
3,884,967  5/1975  Kyburz et al. .......... 260/570.8 TC X Primary Examiner—Richard L. Raymond
Attorney, Agent, or Firm—Samuel L. Welt; George M. Gould; William G. Isgro

[57] ABSTRACT

1-Methyl(or acetyl)-5H-dibenzo[a,d]cycloheptenes and 1-methyl(or acetyl)-10,11-dihydro-5H-dibenzo[a,d]cycloheptenes bearing a basic side chain at the 5-position, such as a 3-mono- or dimethylaminopropylidene, a 3-mono- or dimethylaminopropyl or a 3-dimethylaminopropylidene(or propyl)-N-oxide, intermediates and processes for their preparation, are described. The end products are useful antidepressants.

2 Claims, No Drawings

TRICYCLIC COMPOUNDS

CROSS-REFERENCE TO RELATED APPLICATIONS

This is a division of application Ser. No. 270,674 filed July 11, 1972, which in turn is a continuation-in-part of application Ser. No. 818,146, filed Apr. 21, 1969, now abondoned.

BRIEF SUMMARY OF THE INVENTION

The invention relates to 1-methyl-5-(3-dimethylaminopropylidene)-5H-dibenzo[a,d]cycloheptene N-oxide characterized by the formula

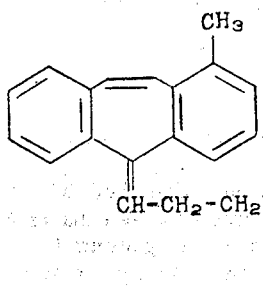
I its geometric and optical isomers and pharmaceutically acceptable acid addition salts thereof. The products are useful as antidepressants.

DETAILED DESCRIPTION OF THE INVENTION

The invention relates to 1-methyl-5-(3-dimethylaminopropylidene)-5H-dibenzo[a,d]cycloheptene N-oxide. In another aspect, the invention relates to intermediates useful in the preparation of compounds characterized by the formulas

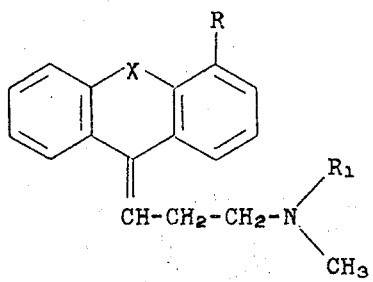
Ia and

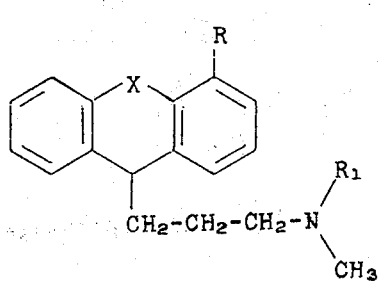
Ib wherein $R_1$ is hydrogen or methyl; R is methyl or acetyl, and X is ethylene ($-CH_2-CH_2-$) or vinylene ($-CH=CH-$) as well as the N-oxides of the compounds of formulas Ia and Ib in which $R_1$ is methyl, i.e., compounds of the formulas

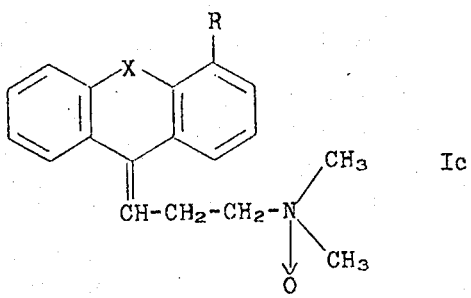
Ic and

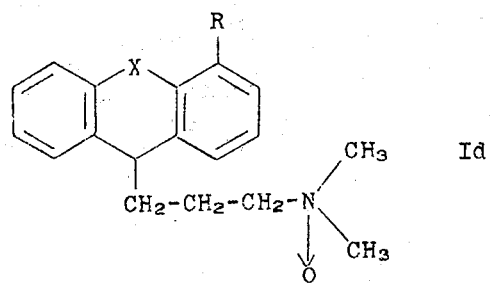
Id their geometric and optical isomers and pharmaceutically acceptable acid addition salts.

The foregoing 1-methyl-5-(3-dimethylaminopropylidene)-5-H-dibenzo[a,d]cyclohehptene N-oxide is distinguished by a considerably increased antidepressive action and reduced toxicity. The absence of substantial anticholinergic action in the said compound is also particularly advantageous. Other aspects of the invention comprise intermediates and processes for the preparation of the compounds of formulas Ia and Ib and their N-oxides.

Exemplary of the compounds of formulas Ia and Ib and the aforementioned N-oxides are the following:
1-methyl(or acetyl)-10,11-dihydro-5-(3-dimethylaminopropylidene)-5H-dibenzo[a,d]cycloheptene;
1-methyl(or acetyl)-10,11-dihydro-5-(3-dimethylaminopropyl)-5H-dibenzo[a,d]cycloheptene;
1-methyl(or acetyl)-10,11-dihydro-5-(3-methylaminopropylidene)-5H-dibenzo[a,b]cycloheptene;
1-methyl(or acetyl)-10,11-dihydro-5-(3-methylaminopropyl)-5H-dibenzo[a,d]cycloheptene;
1-methyl(or acetyl)-5-(3-dimethylaminopropylidene)-5H-dibenzo[a,d]cycloheptene;
1-methyl(or acetyl)-5-(3-dimethylaminopropyl)-5H-dibenzo [a,d]cycloheptene;
1-methyl(or acetyl)-5-(3-methylaminopropylidene)-5H-dibenzo [a,d]cycloheptene;
1-methyl(or acetyl)-5-(3-methylaminopropyl)-5H-dibenzo [a,d]cycloheptene;

1-methyl(or acetyl)-10,11-dihydro-5-(3-dimethylaminopropyl)-5H-dibenzo[a,d]cycloheptene N-oxide;

1-methyl(or acetyl)-5-(3-dimethylaminopropylidene)-5H-dibenzo[a,d]cycloheptene N-oxide and 1-methyl(or acetyl)-10,11-dihydro-5-(3-dimethylaminopropylidene)-5H-dibenzo[a,d]cycloheptene N-oxide.

As used herein, the term "lower alkyl" denotes a straight or branched chain hydrocarbon group containing 1–7 carbon atoms, e.g., methyl, ethyl, propyl, isopropyl, butyl, tertiary butyl, pentyl, heptyl, and the like. The term "lower alkoxy" denotes lower alkyl ether groups in which the lower alkyl moiety is as described above. The term "halogen" denotes all the halogens, i.e., bromine, chlorine, fluorine and iodine. Bromine and chlorine are preferred. The term "acyl" denotes aliphatic and aromatic acyls, for example, lower alkanoyls, such as acetyl, propionyl, butyryl and the like; benzoyl and substituted benzoyl such as halobenzoyl and the like. The term "ketalized acetyl" denotes aliphatic and alicyclic ketalized acetyl, for example, 1,1-dilower alkoxy ethyl, 2-methyl-1,3-dioxolan-2-yl and the like.

A process of the invention for preparing the tricyclic compounds of formulas Ia and Ib, as well as of N-oxides of the compounds of formulas Ia and Ib wherein $R_1$ is methyl, and their geometric and optical isomers and pharmaceutically acceptable acid addition salts, comprises reducing a compound of the formula

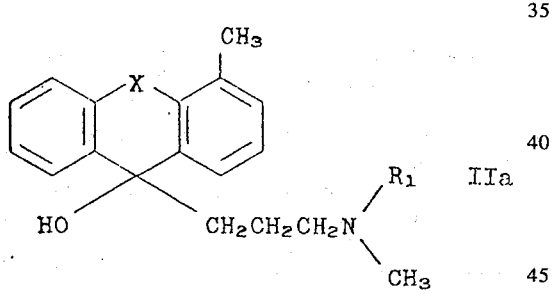

IIa wherein $R_1$ and X are as previously described.

Another process comprises dehydrating a compound of formula IIa, a compound of the formula

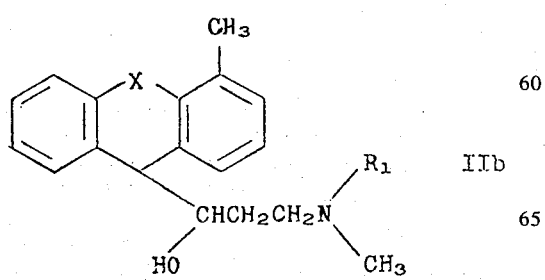

IIb wherein $R_1$ and X are as previously described,
or an N-oxide of formula IIa or IIb wherein $R_1$ is methyl.

Still another process comprises reacting a compound of the formula

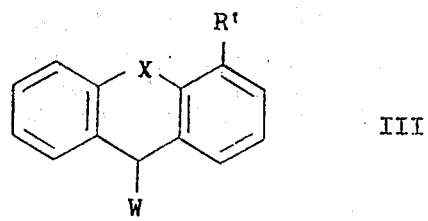

III wherein X is as previously described; R' is methyl or a ketalized acetyl group and W is halogen, with a dimethylaminopropyl magnesium halide.

A still further process comprises treating a compound of the formula

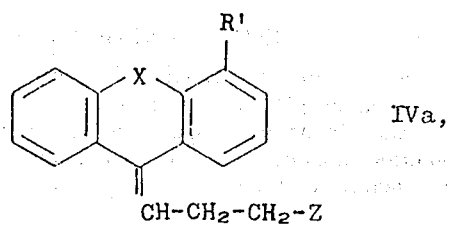

IVa,

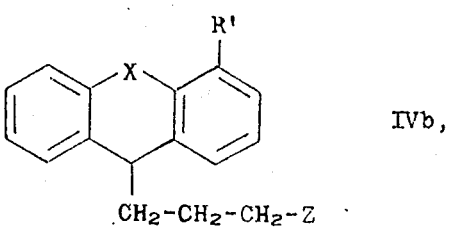

IVb,

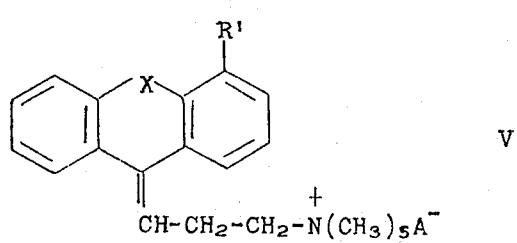

V or

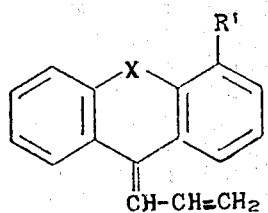

VI

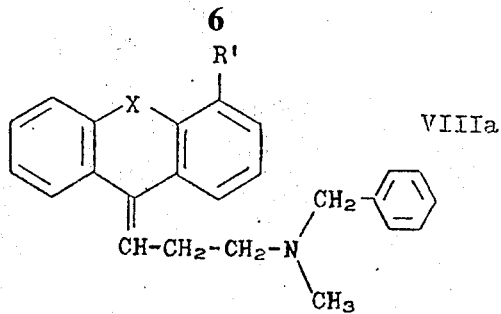

VIIIa or

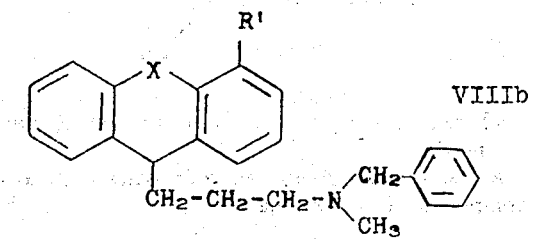

VIIIb wherein R' and X are as previously described; Z is halogen or a substituted sulfonyloxy residue and A is the anion of an acid,
with methylamine, dimethylamine or dimethylhydroxylamine.

Yet another process comprises methylating a primary amine of the formula

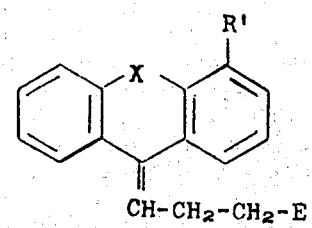

VIIa wherein R' and X are as previously described.

Yet still another process comprises heating a compound of the formula

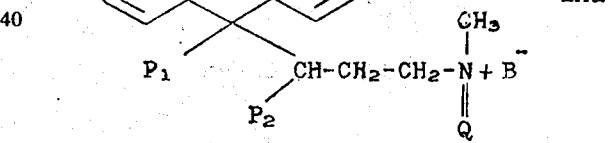

IXa or or

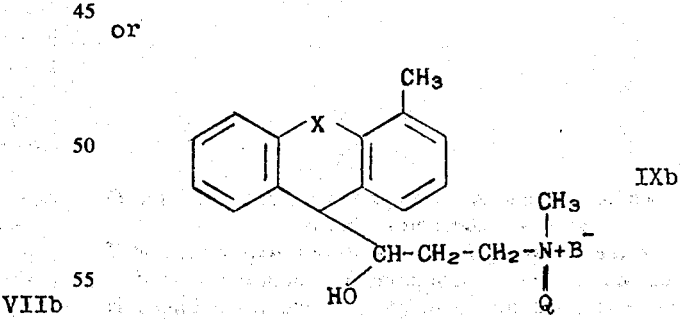

IXb

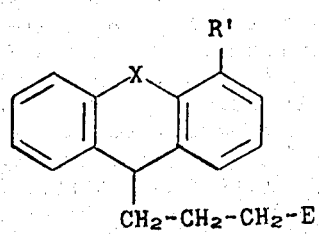

VIIb wherein R' and X are as previously described and E is amino or N-hydroxy-N-methylamino.

A further process comprises debenzylating a compound of the formula wherein R' and X are as previously described; $P_1$ is hydrogen or hydroxyl; and $P_2$ is hydrogen, or $P_1$ and $P_2$ taken together are an additional bond, Q is a residue of an aldehyde and B is the anion of an acid.

An additional process comprises reacting a compound of the formula

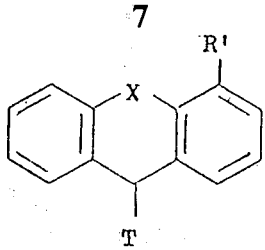

X wherein R' and X are as previously described and T is alkali metal,
with a compound of the formula

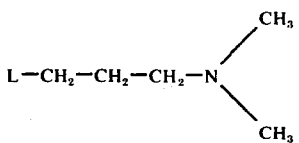

XI wherein L is halogen or a substituted sulfonyloxy residue.

A last process comprises hydrolytically cleaving a compound of the formula

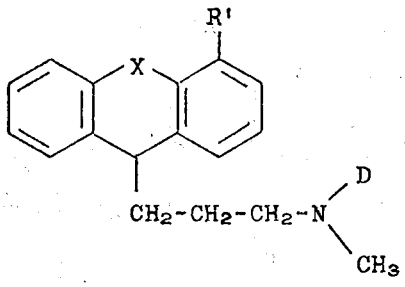

XII wherein R' and X are as previously described and D is acyl or an esterified carboxyl.

In the foregoing processes, in any sequence, and if desired, a monomethylamino compound obtained is methylated; a dimethylamino compound obtained is oxidized or converted into a monomethylamino compound by demthylation; an unsaturated product obtained is hydrogenated; a 10,11-dihydro compound is dehydrogenated; a ketal obtained is deketalized if necessary; the geometric and/or optical isomers are isolated from an isomer mixture obtained; and a base obtained is converted into a pharmaceutically acceptable acid addition salt.

Of the starting compounds of formulas IIa and IIb and the N-oxides of dimethylamino compounds of formulas IIa and IIb, those of formula IIa (and the corresponding N-oxides) are preferably employed.

The reduction of compounds of formula IIa leads to exocyclically saturated compounds of formula Ib. The reduction may conveniently be carried out with catalytically activated hydrogen, for example, in the presence of palladium-charcoal or platinum dioxide. The reaction can be effected in a lower alkanol such as methanol, ethanol or isopropanol, at a temperature in the range of between about room temperature and about 100°C. If desired, the reduction can be conducted under pressure. A compound of formula IIa can also be reduced with zinc in glacial acetic or, preferably, with hydroiodic acid in the presence of red phosphorus. In this reduction, it is preferable to work in the presence of a solvent such as acetic acid or acetic acid anhydride at a temperature in the range of between about room temperature and the boiling point of the reaction mixture. This reduction of compounds of formula IIa yields chiefly compounds of formula Ib which are saturated in the 10,11-position.

The dehydration of compounds of formulas IIa and IIb and the N-oxides of dimethylamino compounds of formulas IIa and IIb leads to compounds of formula Ia which have an exocyclic double bond in the 5-position. The dehydration is conveniently carried out utilizing a mineral acid such as hydrochloric or hydrobromic acid in an anhydrous or aqueous medium. The dehydration is preferably carried out in ethanolic hydrochloric acid at a temperature in the range of between about room temperature and the boiling point of the reaction mixture. However, it also proceeds by heating, for example, at 50°C. up to reflux temperature, preferably at reflux temperature, with a high-boiling anhydrous solvent such as dimethylsulfoxide. Other usual dehydrating agents can also be employed, for example, acetic acid anhydride or sulfuric acid. Conveniently, the temperature is in the range of between about room temperature and the boiling point of the reaction mixture.

When employing an acidic medium in the above reaction, a ketalized acetyl group which may be present is deketalized. On the other hand, by employing, for example, dimethylsulfoxide, the ketal protecting group is retained and can subsequently be split off as hereinafter set forth.

The carbinol of formula IIa or IIb employed in the above reaction can be obtained, for example, in a known manner by reacting the corresponding tricyclic 5-ketone with a suitable Grignard compound. The tricyclic 5-ketones can be obtained according to methods which are known (see the examples hereinafter).

The preparation of a 1-acetylated 5-ketone is effected, for example, in the following manner.

The corresponding tricyclic 1-brominated 5-ketone is heated with copper cyanide in pyridine or quinoline, the bromine being replaced by a cyano group. The nitrile thus obtained is converted by alkaline hydrolysis to the corresponding carboxylic acid. The carboxylic acid is converted into the corresponding acid chloride with a halogenating agent such as thionyl chloride which, after treatment with a methyl cadmium halide such as the chloride, forms the corresponding 1-acetyl-5H-dibenzo[a,d]cyclohepten-5-one or 1-acetyl-10,11-dihydro-5H-dibenzo[a,d]cyclohepten-5-one. The acetyl group can then be ketalized in a known manner, for example, by treating the compound obtained with a lower alkanol or glycol, preferably methyl alcohol or ethylene glycol. An additional method for preparing 1-acetylated 5-ketones is described in Example 16.

Carbinols of formula IIa are conveniently obtained as follows.

If a carbinol of formula IIa wherein $R_1$ is methyl is to be prepared, a corresponding tricyclic 5-ketone is reacted directly, for example, with dimethylaminopropyl magnesium chloride and subsequently the reaction product is hydrolyzed. If $R_1$ is hydrogen, it is preferred to use methyl-benzylaminopropyl magnesium chloride as the reagent for the reaction. After completion of the reaction and subsequent hydrolysis, the resulting product is reacted with ethyl chloroformate and the resulting 5-hydroxy-5-[3-(methyl-carbethoxy-amino)-propyl] compound is hydrolyzed whereby a spontaneous decarboxylation occurs with the formation of the corresponding 5-hydroxy-5-(3-methylaminopropyl) compound.

Carbinols of formula IIb are obtained, for example, by reacting the corresponding tricyclic 5-ketone with ethyl magnesium bromide and hydrolyzing the reaction product. The resulting 5-hydroxy-5-ethyl compound is dehydrated with acetyl chloride and subsequently treated with formic acid and hydrogen peroxide whereby a 5-hydroxy-5-(1-hydroxyethyl) compound is obtained which is dehydrated with aqueous sulfuric acid to the corresponding 5-acetyl compound. By treatment with formaldehyde and methyl- or dimethylamine hydrochloride, there is obtained a 5-(methyl- or dimethylaminopropionyl) compound which, after reduction with sodium borohydride, yields the corresponding carbinol.

The carbinols of formulas IIa and IIb obtained above wherein $R_1$ is methyl can be converted to the corresponding N-oxides by oxidation which are likewise employable as starting compounds. The oxidation can, for example, be carried out by treatment with hydrogen peroxide in a solvent such as, for example, methanol or ethanol, at a temperature in the range of about room temperature and the boiling point of the reaction mixture.

According to another process of the invention, a halide of formula III is reacted with a dimethylaminopropyl magnesium halide, whereby the exocyclically saturated compounds of formula Ib are obtained. It is particularly suitable for the preparation of those exocyclically saturated compounds of formula Ib which simultaneously carry a double bond in the 10,11-position. According to a preferred embodiment of this process, a compound of formula III wherein W is chlorine, either as a solid, fine powder or in inert organic solvents such as, for example, absolute ether, benzene, tetrahydrofuran or the like, is introduced to a suspension of dimethylaminopropyl magnesium chloride in one of the inert solvents above mentioned. The reaction is conveniently conducted at a temperature in the range of between about room temperature and the boiling point of the reaction mixture.

The starting halide of formula III can be obtained according to methods which are known, for example, by the reduction of the corresponding tricyclic 5-ketone and subsequent halogenation of the resulting 5-hydroxy compound. Products deketalized in the 1-position which are obtained after the halogenation can again be ketalized as described above.

A further process of the invention comprises treating a compound of formula IVa, IVb, V or VI with methylamine, dimethylamine or dimethylhydroxylamine.

In the above formulas IVa and IVb, Z preferably is chlorine or bromine. Substituted sulfonyloxy residues as Z are preferably lower alkylsulfonyloxy such as mesyloxy; phenylsulfonyloxy; lower alkylphenylsulfonyloxy such as tosyloxy; or phenyl-lower alkylsulfonyloxy such as phenylmesyloxy. The anion A is preferably derived from an inorganic acid such as hydrochloric acid, hydrobromic acid, hydroiodic acid or sulfuric acid.

The reaction of the compounds of formulas IVa, IVb, V and VI with methylamine, dimethylamine or dimethylhydroxylamine is conveniently conducted in a closed vessel at an elevated temperature, for example at a temperature in the range of about 50° and about 175°C. The reaction can be effected in an inert organic solvent such as methanol, ethanol, benzene, toluene or the like. It is preferred to utilize an excess of methylamine, dimethylamine or dimethylhydroxylamine. In the reaction with compounds of formulas IVa and IVb, the excess serves as an acid-binding agent. Other acid-binding agents can, however, also be employed, for example, anhydrous potassium carbonate. The compounds of formula VI are preferably reacted in the presence of a metal-organic compound such as, for example, phenyl lithium or a Grignard compound. The use of a Grignard compound is particularly advantageous.

In the case of the reaction with dimethylhydroxylamine, when R' is a methyl group, there results an N-oxide of a dimethylamino compound of formula Ia or Ib.

A ketalized 1-acetyl group which may be present is retained after the reaction with dimethylhydroxylamine and must subsequently, as hereinafter illustrated, be deketalized to form the corresponding N-oxide of a dimethylamino compound of formula Ia or Ib.

The starting compound of formulas IVa and IVb may, for example, be prepared by reacting the corresponding tricyclic 5-ketone with a methoxypropyl magnesium halide and subsequent hydrolysis. After dehydration of the resulting carbinol and treatment of the resulting product with a halogenating agent or (after hydrolysis in a manner known per se) with a sulfonylating agent, there is obtained the corresponding exocyclically unsaturated product of formula IVa.

Exocyclically saturated compounds of formula IVb can be prepared, for example, by reacting a compound of formula III with a methoxypropyl magnesium halide. The resulting 5-(3-methoxypropyl) compound is subsequently converted by treatment with a halogenating agent or (after hydrolysis in a manner known per se) with a sulfonylating agent to the corresponding exocyclically saturated starting compound of formula IVb. The 1-position deketalized compounds, obtained in the above reaction, can be ketalized as described hereinabove.

The quaternary salt of formula V which is also employable as the starting material can be obtained by quaternization of the corresponding amino, monomethylamino or dimethylamino compound with a methylating agent such as methyl chloride, methyl bromide, methyl iodide, dimethylsulfate or the like.

The starting compound of formula VI is, for example, obtainable from the corresponding tricyclic 5-ketone by reaction with an allyl Grignard compound.

According to another process of the invention, a compound of formula VIIa or VIIb is methylated. The methylation can be effected with a usual methylating agent such as, for example, methyl iodide, methyl tosylate, dimethylsulfate or the like, preferably at a temperature in the range of between about 15° and 75°C. According to another procedure, a mixture of formaldehyde and formic acid, preferably in excess at an elevated temperature, for example, in the range of between about 50°C. and the boiling point of the reaction mixture, is reacted with a primary amine of formula VIIa or VIIb. A ketalized acetyl group which may be present is thereby deketalized. A preferred embodiment for the preparation of secondary amines of formulas Ia and Ib comprises reacting a primary amine of formula VIIa or VIIb with a haloformic acid ester, for example, ethyl chloro- or bromoformate to give a carbamate which is subsequently reduced with a metal hydride such as lithium aluminum hydride, diisobutyl aluminum hydride or the like. Both reaction steps are preferably carried out in an inert solvent such as ether or tetrahydrofuran, at a temperature in the range of between about room temperature and the reflux temperature of the reaction mixture, preferably at reflux temperature. According to another method for preparing the secondary amines of formula Ia or Ib, the corresponding primary amine of formula VIIa or VIIb is reacted with chloral, preferably in inert solvent such as chloroform or benzene at an elevated temperature, for example, in the range of between about 50°C. and the boiling point of the reaction mixture. The resulting formylamino compound is reduced to the corresponding secondary amine of formula Ia or Ib with a metal hydride such as lithium aluminum hydride in anhydrous ether. A further method for the preparation of the secondary amines of formula Ia or Ib comprises the reaction of the corresponding primary amine of formula VIIa or VIIb with formaldehyde, preferably in an inert solvent such as benzene or toluene, at a temperature in the range of between about room temperature and the boiling point of the reaction mixture. The resulting Schiff's base is subsequently converted into the corresponding secondary amine of formula Ia or Ib by reduction. The reduction is conveniently effected with catalytically activated hydrogen, for example, with hydrogen in the presence of palladium-charcoal, nickel or platinum dioxide, or especially when the double bond present, as well as ketalized 1-acetyl group which may be present, is to be retained, with a metal hydride such as sodium borohydride or lithium aluminum hydride in anhydrous ether or dioxane.

When employing the N-hydroxy-N-methylamino compounds of formula VIIa or VIIb, they are chiefly reacted with one of the usual methylating agents mentioned above, for example, methyl iodide, methyl tosylate, dimethylsulfate or the like, whereby there results the N-oxides of the corresponding dimethylamino compounds of formula Ia or Ib. A ketalized acetyl group R' which may be present in the starting compound is retained in this reaction and must subsequently be deketalized as explained later.

The starting compounds of formulas VIIa and VIIb can be obtained in several ways. Aminopropylidene compounds of formula VIIa or VIIb are, for example, obtained by exchange of the keto group of the corresponding 5-ketone for an ethylidene group, for example, by means of a Grignard reagent, subsequent halogenation, treatment with a cyanide and reduction with lithium aluminum hydride. The reduction can also be conducted on a compound possessing a 1-methyl group with catalytically activated hydrogen whereby the corresponding aminopropyl compound of formula VIIa or VIIb is obtained.

The compounds of formulas VIIa and VIIb wherein E is amino, are also obtained by treating the corresponding compounds of formula IVa or IVb with potassium phthalimide and the reaction of the product obtained with hydrazine. Exocyclically saturated starting compounds of formulas VIIa and VIIb, wherein E is amino, are also obtained for instance by reacting a compound of formula X with acrylonitrile and subsequently reducing the nitrile group, for example, with lithium aluminum hydride.

The tricyclic hydroxylamine of formulas VIIa and VIIb which serve as the starting materials can, for example, be prepared by the following reaction sequence.

1-Methyl(or ketalized acetyl)-5H-dibenzo[a,d]cyclohepten-5-one or the corresponding 10,11-dihydro compound is reacted with a methylbenzylaminopropyl magnesium halide. After hydrolysis of the resulting addition product, for example, with a saturated ammonium chloride solution, the 5-carbinol obtained is reacted with ethyl chloroformate. The 5-hydroxy-5-[3-(methyl-carbethoxyamino)-propyl] compound thus obtained is then hydrolyzed with an alkali, for example, by boiling with aqueous potassium hydroxide solution. A decarboxylation occurs and the corresponding 5-hydroxy-5-(3-methylaminopropyl) compound is formed which can be reduced, if it possesses a methyl group in the 1-position of the ring system, to the corresponding 5-(3-methylaminopropyl) compound by treatment with catalytically activated hydrogen, for example, in the presence of palladium-charcoal or platinum dioxide. If, on the other hand, the resulting 5-hydroxy-5-[3-methyl-carbethoxyamino-propyl] compound is heated with mineral acid, for example, with ethanolic hydrochloric acid, there results the corresponding 5-(3-methylaminopropylidene) compound. Deketalized acetyl groups are subsequently again ketalized. Then, the reaction product can be treated at about 0°C. with benzoyl peroxide, for example, in an organic solvent such as ether or chloroform. The methylbenzoyloxy-amino-propyl-(idene) compound thus obtained can be converted into the desired tricyclic hydroxylamine of formula VIIa or VIIb by simple saponification with alkali such as, for example, ethanolic caustic potash.

According to a further process of the invention, a compound of the formula VIIIa or VIIIb is debenzylated. In the debenzylation, the benzyl group attached to the nitrogen atom is exchanged for a hydrogen atom whereby there results the corresponding secondary amine of formula Ia or Ib. This reaction is conveniently carried out by reduction with an alkali metal such as sodium or lithium in liquid ammonia. After this procedure, double bonds which may be present are substantially retained.

The debenzylation can also be effected by treating a compound of formula VIIIa or VIIIb with a haloformic acid ester and hydrolyzing the resulting carbamate. The alcoholic portion of the haloformic acid ester utilized is preferably derived from the following alcohols: lower alkanols such as methanol, ethanol, isopropanol; phenol; or lower phenylalkanols such as benzyl alcohol. The halogen atom is preferably chlorine. The reaction with haloformic acid ester proceeds conveniently in a high-boiling inert solvent such as xylene or toluene, and at a temperature in the range of between about 50° and the reflux temperature of the reaction mixture, preferably at the reflux temperature. The subsequent hydrolysis can be effected in alkaline or acidic conditions, for example, with the aid of potassium hydroxide in butanol or hydrogen bromide in glacial acetic acid and at a temperature in the range of between about 50°C. and the boiling point of the reaction mixture.

The starting compounds of formulas VIIIa and VIIIb are conveniently obtained by reacting one of the corresponding compounds of formula IVa, IVb, V or VI with methylbenzylamine.

A further process of the invention comprises heating a compound of the formula IXa or IXb. If desired, the reaction can be effected in the presence of aqueous acid such as sulfuric acid. Carbinols of formula IXa or IXb which may be employed in this reaction are dehydrated and ketalized 1-acetyl groups present are deketalized. The substituent Q is simultaneously removed whereby the corresponding secondary amines of formula Ia or Ib are formed. In formulas IXa and IXb, Q is, for example, the residue $R_2CH=$, wherein $R_2$ is alkyl, phenyl, phenylalkyl, alkylphenyl or alkoxyphenyl and the alkyl, as well as the alkoxy groups, contain 1 to 7 carbon atoms. Q preferably is benzylidene.

The residue B preferably is the anion of a strong inorganic or organic acid, for example, the anion of hydrochloric acid, sulfuric acid, methanesulfonic acid, benzenesulfonic acid or preferably the anion of toluenesulfonic acid. According to a preferred embodiment, a compound of formula IXa wherein $P_1$ is hydroxy and $P_2$ is hydrogen, is reacted with aqueous sulfuric acid at a temperature in the range of between about 50° and 150°C.

The starting compounds of formula IXa and IXb are, for example, obtained by reacting the corresponding 5-hydroxy-5-(3-aminopropyl) compound, prepared by the reaction of the corresponding 5-ketone with an alkali metal and subsequent treatment of the resulting alkali metal compound with an aminopropyl halide, with the corresponding 5-(3-amino-1-hydroxypropyl) compound, prepared by the reaction of the corresponding 5-acetyl compound with formaldehyde and ammonium chloride, followed by reduction with sodium borohydride or the corresponding compound of formula VIIa or VIIb with an aldehyde such as benzaldehyde, and quaternizing the resulting Schiff's base with a methylating agent such as methyl chloride, dimethylsulfate, methyl mesylate, methyl benzenesulfonate or, especially methyl tosylate at elevated temperature. The compounds of formulas IXa and IXb thus obtained can be further processed without further purification. Often it is desirable not to isolate them, but to immediately react the reaction mixture with aqueous acid at an elevated temperature as discussed above.

A still further process of the invention comprises the reaction of a compound of formula X with a compound of formula XI. By this reaction, there are obtained the exocyclically saturated compounds of formula Ib. In formula X, the symbol T preferably is sodium, potassium or lithium. L in formula XI is preferably chlorine. In its significance as a substituted sulfoxy residue, L preferably is a lower (cyclo-) alkylsulfonyloxy such as mesyloxy, cyclopropylsulfonyloxy; phenylsulfonyloxy; a lower alkylphenylsulfonyloxy such as tosyloxy; or phenyl-lower alkylsulfonyloxy such as phenylmesyloxy. The reaction is conveniently carried out in an inert solvent such as benzene, toluene, hexane, heptane, ether or the like, at a temperature in the range of between about room temperature and the boiling point of the reaction mixture.

The starting compounds of formula X employed in the above reaction can, for example, be obtained by treatment of the corresponding 5-ketone or 5-hydroxy compound (after previous ketalization of a 1-acetyl group which may be present) with aluminum isopropoxide and subsequent reaction with an alkali metal amide or hydride. A suitable method for the preparation of the starting compounds of formula X in which R' is a ketalized acetyl group comprises the following: 1 mole of o-cyano-benzyl chloride is converted to the corresponding Grignard and treated with 1 mole of o-cyano-benzyl chloride. After hydrolysis, the resulting $\alpha,\alpha'$-bis-o-toluene nitrile is converted to the corresponding bis-acid with alkali hydroxide and ethylene glycol and treated with polyphosphoric acid. The resulting 1-carboxy-10,11-dihydro-5H-dibenzo[a,d]cyclohepten-5-one is converted to the corresponding 5-hydroxy compound with sodium borohydride in dioxane, which is transformed to the 5-unsubstituted compound with hydroiodic acid and red phosphorus and later to the corresponding 1-chlorocarbonyl compound. The latter compound is treated with a salt such as the magnesium salt of a malonic acid ester. By decomposition of the product obtained with aqueous hydrochloric acid, 1-acetyl-10,11-dihydro-5H-dibenzo[a,d]cycloheptene is obtained, which is ketalized in the usual manner. The resulting product is converted with the aid of an alkali metal amide or hydride to the corresponding starting compound of formula X.

According to yet another process of the invention, compounds of formula XII are hydrolytically cleaved, whereby the corresponding secondary amines of formulas Ia and Ib are obtained. The group D can, for example, be acyl such as lower alkanoyl, for example, formyl, acetyl, or the like; phenyl-lower alkanoyl, for example, benzoyl; lower alkylsulfonyl, for example, mesyl; phenylsulfonyl; lower alkylphenylsulfonyl, for example, tosyl; or phenyl-lower alkylsulfonyl, for example, phenylmesyl. In its significance as an esterified carboxy group, the D preferably is lower carbalkoxy such as carbomethoxy, carbethoxy, carboisopropoxy or the like; carbophenoxy; or lower carbophenylalkoxy such as carbobenzoxy. In the case where D is a non-sulfur-containing group, the cleavage proceeds under the conditions which are usual for acidic or alkaline hydrolysis, for example, with heating, i.e., at a temperature in the range of between about 50°C. and the boiling point of the reaction mixture in the presence of an ethanolic solution of hydrochloric acid, acetic acid, sodium hydroxide or potassium hydroxide. The alkaline hydrolysis is preferred. In the case where B is a sulfur-containing group, it is desirable to carry out the cleavage by treatment, for example, with hydrobromic acid in acetic acid in the presence of phenol or with an alkali metal and a high-boiling alcohol, for example, sodium and butanol. Such reactions are conveniently effected with heating at a temperature in the range of between about 50°C. and the boiling point of the reaction mixture. Another method for the cleavage of sulfur-containing groups comprises treating with liquid ammonia and an alkali metal such as sodium. In the case of alkaline hydrolysis, ketalized 1-acetyl groups are subsequently deketalized as explained hereinafter.

The starting compound of formula XII can, for example, be obtained by heating a compound of formula X in ether with a methyl-D-aminopropyl halide wherein the symbol D is as previously described.

The compounds of formulas Ia and Ib prepared in the manner stated above can, if desired, be subjected to additional transformations.

A methylamino compound of formula Ia or Ib or corresponding compound containing a ketalized 1-acetyl group can be transformed into a dimethylamino compound according to methods which are known, for example, by treatment with a methylating agent such as methyl iodide, methyl mesylate, methyl tosylate or dimethylsulfate, preferably at a temperature in the range of between about 15° and about 75°C. According to another procedure, a mixture of formaldehyde and formic acid, preferably in excess and at an elevated temperature, for example, in the range of between about 50°C. and the boiling point of the reaction mixture, is reacted with a methylamino compound of formula Ia or Ib. It is also possible, when R is methyl, to react a methylamino compound of formula Ia or Ib with formaldehyde and hydrogen at about room temperature in the presence of a catalyst such as palladium-charcoall, Raney-nickel or platinum dioxide.

Dimethylamino compounds of formulas Ia and Ib or the corresponding compounds containing a ketalized 1-acetyl group can be transformed into the corresponding monomethylamino compounds. A particularly suitable embodiment of this transformation comprises reacting the aforementioned dimethylamino compounds with a cyanogen halide, preferably with cyanogen bromide. The reaction is conveniently carried out in an inert solvent such as, for example, benzene, ether, tetrahydrofuran or methylene chloride and at a temperature in the range of between room temperature and the boiling point of the mixture. The resulting N-cyano-N-methylamino compound is subsequently hydrolyzed in a known manner in an alkaline or acidic medium, the monomethylamino compound of formula Ia or Ib being formed as the base or as an acid addition salt depending upon the hydrolysis medium used.

According to another embodiment for the demethylation of dimethylamino compounds of formulas Ia and Ib or of the corresponding compounds containing a ketalized 1-acetyl group, said compounds are treated with a haloformic acid ester and the resulting carbamate is hydrolyzed. The alcoholic portion of the haloformic acid ester which is to be introduced is preferably derived from the following alcohols: a lower alkanol such as methanol, ethanol or isopropanol; phenol; or a lower phenylalkanol such as benzyl alcohol. The halogen atom conveniently is chlorine. The reaction with the haloformic acid ester is conveniently effected in a high-boiling inert solvent such as xylene or toluene and at a temperature in the range of between about 50°C. and the reflux temperature of the reaction mixture, preferably at reflux temperature. The subsequent hydrolysis can be carried out under alkaline or acidic conditions, for example, with the aid of potassium hydroxide in butanol or hydrogen bromide in glacial acetic, and at a temperature in the range of between about 50°C. and the boiling point of the reaction mixture.

By oxidation of a dimethylamino compound of formula Ia or Ib or of a corresponding compound containing a ketalized 1-acetyl group, the corresponding N-oxides can be obtained. Various compounds which readily release oxygen serve as the oxidizing agent, for example, organic peroxides, such as monosubstituted organic peroxides, for example, $C_1$-$C_4$ alkylhydroperoxides such as t-butyl hydroperoxide as well as phenyl-substituted derivatives of $C_1$-$C_4$ alkyl hydroperoxides such as cumyl hydroperoxide. If desired, the phenyl substituent can carry an additional lower $C_1$-$C_4$ alkyl or alkoxy or halogen. As the oxidizing agent there can also be used various inorganic oxidizing agents, for example, hydrogen peroxide; ozone; hypochlorites such as sodium, potassium or ammonium hypochlorite; peroxymono- and peroxydisulfuric acid. The use of hydrogen peroxide is preferred. The oxidation is advantageously effected in a solvent, for example, methanol, ethanol, ether, benzene or chloroform, at a temperature in the range of between about −50°C. and +100°C. After a work up in the usual manner, with the removal of the excess oxidizing agent, there is obtained the corresponding N-oxide. The latter is conveniently recovered in the form of an acid addition salt.

Compounds of formulas Ia and Ib, in which R is methyl and which carry a double bond in the exocyclic 5-position and/or in the 10,11-position can be hydrogenated. The double bond in the 10,11-position is more readily hydrogenable than that in the exocyclic 5-position so that insofar as both are simultaneously present, the reaction can be used for the selective hydrogenation of the double bond in the 10,11-position. The hydrogenation proceeds, for example, at about room temperature with the aid of hydrogen in the presence of a catalyst such as Raney-nickel, palladium-charcoal or platinum dioxide.

10,11-Dihydro compounds of formulas Ia and Ib or the corresponding compounds containing a ketalized 1-acetyl group can be dehydrogenated in the 10,11-position. This is conveniently effected by heating for example in the range of between about 150° and 250°C., with a catalyst such as palladium-charcoal, Raney-nickel or platinum dioxide, conveniently in an inert solvent, such as tetrahydronaphthalene or diethyleneglycol monomethylether.

According to another procedure for the dehydrogenation of 10,11-dihydro compounds of formulas Ia and Ib or of corresponding compounds containing a ketalized 1-acetyl group, after the introduction of a protecting group into a monomethylamino group which may be present, by halogenation there is introduced into the 10- or 11-position a halogen atom which, as explained later, can be split off with the formation of a 10,11-double bond. After splitting off the protecting group which may be present, there is obtained a compound of formula Ia or Ib which is unsaturated in the 10,11-position or a corresponding compound containing a ketalized 1-acetyl group.

Representative examples of suitable protecting groups are: cyanide or an esterified carboxy such as carbomethoxy, carbethoxy, carboisopropoxy, carbophenoxy and carbobenzoxy. The cyanide group is conveniently introduced by reacting with a cyanogen halide, preferably with cyanogen bromide, for example in an inert solvent such as benzene, ether, tetrahydrofuran or methylene chloride at a temperature in the range of between about room temperature and the boiling point of the reaction mixture. The introduction of the esterified carboxy group is effected, for example, by reaction with a corresponding haloformic acid ester such as a chloroformic acid ester. This reaction is preferably effected in an inert solvent such as chloroform, xylene or toluene at a temperature in the range of between about room temperature and the boiling point of the reaction mixture. If a monomethylamino compound of formula Ia or Ib is employed for the introduction of the cyanide group or of an esterified carboxy group, it is desirable to add an acid-binding agent such as triethylamine or pyridine. The reaction then proceeds particularly rapidly, often at room temperature.

An additional protecting group which is suitable for introduction into a monomethylamino compound of formula Ia or Ib is the acyl group derived from a lower carboxylic acid such as acetyl, isobutyryl, benzoyl or phenylacetyl. The introduction of such a protecting group is effected, for example, by reaction of a monomethylamino compound of formula Ia or Ib with acetyl chloride or acetic anhydride, conveniently in the presence of an acid-binding agent such as triethylamine or pyridine. The reaction can be effected in the range of between about room temperature and the reflux temperature of the reaction mixture, although room temperature is often sufficient.

The compound obtained, protected at the nitrogen atom if necessary, is subsequently treated with a halogenating agent such as N-bromosuccinimide, N-chlorosuccinimide, bromine, chlorine or sulfuryl chloride, whereby a halogen atom is added in the 10- or 11-position. This reaction is preferably effected in an inert solvent such as carbon tetrachloride, benzene, heptane, chloroform or tetrahydrofuran at elevated temperature, for example, in the range of about 50° C. and the boiling point of the reaction mixture. It is very advantageous to add a small amount of a reaction promoter such as azo-bis-butyronitrile or dibenzoyl peroxide, as well as a hydrogen halide acceptor, for example, pyridine, triethylamine, collidine, allyl chloride or an epoxide. The resulting 10,11-dihydro compound halogenated in the 10- or 11-position is subsequently treated with a basic agent such as sodium hydroxide, potassium carbonate or triethylamine, at a temperature in the range of between about room temperature and the boiling point of the reaction mixture, whereby the 10,11-double bond is formed with the splitting off of hydrogen halide. The protecting group which, if necessary, is linked to the nitrogen atom is then hydrolytically split off in the manner described earlier whereby an amine of formula Ia or Ib which is unsaturated in the 10,11-position or a corresponding compound containing a ketalized 1-acetyl group is obtained.

The deketalization of the ketalized 1-acetyl group is conveniently effected by treatment of the product with a dilute acid such as hydrochloric acid or sulfuric acid at a temperature in the range of between about room temperature and the boiling point of the reaction mixture. The reaction may be carried out in the presence of a lower alkanol such as methanol or ethanol.

Compounds of formulas Ia and Ib which carry an exocyclic double bond and/or a double bond in the 10,11-position and their pharmaceutically acceptable acid addition salts can be separated into their geometric isomers, that is, the α- or β-isomers. The methods of separation are known. The geometric isomers are preferably separated by fractional crystallization of the acid addition salts from a solvent such as acetone or from a solvent mixture such as methanol/diethyl ether.

Compounds of formulas Ia and Ib and their pharmaceutically acceptable acid addition salts exist as racemates. A racemate can be separated into its optical isomers in a known manner, for example, by reaction with optically active acids such as tartaric acid or camphor sulfonic acid and subsequent crystallization.

The separation of the geometric and/or optical isomers can be undertaken at an intermediate-product stage so that in this manner the processes in accordance with the invention are carried out with geometrically or optically uniform starting materials.

The compounds of formulas Ia and Ib have basic character and can be converted into pharmaceutically acceptable acid addition salts. Such salts are, for example, those with organic acids such as oxalic acid, citric acid, acetic acid, lactic acid, maleic acid and tartaric acid, or with inorganic acids such as hydrochloric acid, hydrobromic acid or sulfuric acid. The acid addition salts are crystalline solid substances which are soluble in water, somewhat less soluble in polar solvents such as methanol, ethanol and the like, and relatively insoluble in non-polar solvents such as benzene, ether, petroleum ether and the like.

As mentioned earlier, the compounds of the invention and, specifically, 1-methyl-5-(3-dimethylaminopropylidene)-5H-dibenzo [a,d]cycloheptene N-oxide, possess an excellent antidepressive action. To demonstrate this, a number of compounds of the invention were administered to groups of 5 rats each in three doses of 50 mg/kg. p.o., twice on the day before, once on the day of the experiment. Six hours later, the animals received 20 mg/kg. of 2-hydroxy-2-ethyl-3-isobutyl-9,10-dimethoxy-1,2,3,4,6,7-hexahydro-11bH-benzo[a,d]quinolizine hydrochloride injected subcutaneously. The same dosage was administered to a control group of 5 non-pretreated rats. The ratings include central and peripheral symptoms, which are characteristic for tricyclic antidepressants [cf. Ann. N.Y. Acad. Sci. 96, 279 (1962)]. The suppression of ptosis, seeking behavior, motility and sensitivity to stimulus were observed for the purpose of determining antidepressive action. These changes were recorded according to a rating scheme which utilized numbers.

The compounds as set forth in Table I demonstrated in this test a strong antidepressive action which manifested itself in complete suppression of ptosis as well as in strongly increased characteristic motility, sensitivity to stimulus and seeking behavior. The stated percentages are compared with the values for Amitriptyline* (Amitriptyline 100%).

*5-(3-dimethylaminopropylidene)-dibenzo[a,d][1,4] cycloheptadiene

TABLE I

| Test Compound | Activity in % compared to Amitrintyline |
|---|---|
| 1-Methyl-10,11-dihydro-5-(3-dimethyl-aminopropylidene)-5H-dibenzo[a,d]cycloheptene hydrochloride | 220 |
| 1-Methyl-10,11-dihydro-5-(3-dimethyl-aminopropyl)-5H-dibenzo[a,d]cycloheptane hydrochloride | 180 |
| 1-Methyl-10,11-dihydro-5-(3-methylamino-propylidene)-5H-dibenzo[a,d]cycloheptene hydrochloride | 140 |
| 1-Methyl-10,11-dihydro-5-(3-methylamino-propyl)-5H-dibenzo[a,d]cycloheptene hydrochloride | 180 |
| 1-Methyl-5-(3-dimethylaminopropylidene)-5H-dibenzo[a,d]cycloheptene hydrochloride | 130 |
| 1-Methyl-5-(3-methylaminopropylidene)-5H-dibenzo[a,d]cycloheptene hydrchloride | 230 |
| 1-Methyl-5-(3-dimethylaminopropylidene)-5H-dibenzo[a,d]cycloheptene-N-oxide hydrochloride | 140 |

The low toxicity of the compounds of the invention can be illustrated by the acute toxicity of 1-methyl-10,11-dihydro-5-(3-dimethylaminopropyl)-5H-dibenzo[a,d]cycloheptene hydrochloride in mice (24-hour values):

$LD_{50}$ i.v. = 25–50 mg/kg.
$LD_{50}$ p.o. = 300–600 mg/kg.

The low anticholinergic action can be shown by the lack of salivation inhibition in rabbits: The salivation in rabbits under light urethane narcosis was increased by pilocarpine injection (5 mg/kg. s.c.) and the amount of saliva was measured at 5-minute intervals. The inhibition of salivation is expressed as a percentage based upon the salivation of animals which only received pilocarpine.

The compounds as set forth in Table II demonstrated in this test a low salivation inhibition.

TABLE II

| Test Compound (3 mg/kg. i.v.) | % Inhibition of Salivation |
| --- | --- |
| 1-Methyl-10,11-dihydro-5-(3-dimethyl-aminopropylidene)-5H-dibenzo[a,d]cycloheptane hydrochloride | 50 |
| 1-Methyl-10,11-dihydro-5-(3-dimethyl-aminopropyl)-5H-dibenzo[a,d]cycloheptene hydrochloride | 50 |
| 1-Methyl-10,11-dihydro-5-(3-methyl-aminopropylidene)-5H-dibenzo[a,d]cycloheptene hydrochloride | 50 |
| 1-Methyl-10,11-dihydro-5-(3-methylamino-propyl)-5H-dibenzo[a,d]cycloheptene hydrochloride | 40 |
| 1-Methyl-5-(3-dimethylaminopropylidene)-5H-dibenzo[a,d]cycloheptene hydrochloride | 60 |
| 1-Methyl-5-(3-methylaminopropylidene)-5H-dibenzo[a,d]cycloheptene hydrochloride | 60 |
| 1-Methyl-5-(3-dimethylaminopropylidene)-5H-dibenzo[a,d]cycloheptene-N-oxide hydrochloride | 14 |
| Amitriptyline | 96 |

The products of the invention can be used as medicaments; for example, in the form of pharmaceutical preparations which contain them or their pharmaceutically acceptable acid addition salts in admixture with a pharmaceutical, organic or inorganic inert carrier material which is suitable for enteral such as oral or parenteral application, for example, water, gelatin, lactose, starches, magnesium stearate, talc, vegetable oils, gum arabic, polyalkylene glycols, and the like. The pharmaceutical preparations can be prepared in solid form such as tablets, dragees, suppositories, capsules or in liquid form, such as solutions, suspensions or emulsions. They may be sterilized and/or contain additives such as preserving, stabilizing, wetting or emulsifying agents, salts for varying the osmotic pressure or buffers. They can also contain yet other therapeutically valuable substances.

Convenient pharmaceutical dosage forms contain about 1 to 200 mg. of a compound of the invention. Convenient oral dosages are in the range of about 0.1 mg/kg per day to about 5 mg/kg per day. Convenient parenteral dosages are in the range of about 0.01 mg/kg. per day to about 0.5 mg/kg. per day. However, the ranges mentioned can be extended upwards or downwards depending upon individual requirements.

The following examples further illustrate the invention. All temperatures are in degrees Centigrade, unless otherwise mentioned.

EXAMPLE 1

Preparation of
1-methyl-10,11-dihydro-5-(3-dimethylamino-propylidene)-5H-dibenzo[a,d]cycloheptene 18 g. of 1-methyl-10,11-dihydro-5-(3-dimethylaminopropyl)-5-hydroxy-5H-dibenzo[a,d]cycloheptene and 180 ml. of 3% ethanolic hydrochloric acid are heated on the steam bath under reflux conditions for 2 hours and subsequently evaporated to dryness. The residual 1-methyl-10,11-dihydro-5-(3-dimethylaminopropylidene)-5H-dibenzo[a,d]cycloheptene hydrochloride has a melting point of 216°–220° C. after recrystallization from ethanol-ether and comprises a mixture of the α- and β-isomers. The 1-methyl-10,11-dihydro-5-(3-dimethylaminopropyl)-5-hydroxy-5H-dibenzo[a,d]cycloheptene employed as the starting compound can be prepared as follows.

10 g. of Gilman alloy are covered with 30 ml. of dry ether and treated with 0.5 ml. of methyl iodide. After the vigorous reaction has subsided somewhat, 40 ml. of 1-chloro-3-dimethylaminopropane in 120 ml. of dry ether are added dropwise in such a way that the reaction mixture is maintained at boiling. The mixture is heated at 45° C. under reflux conditions for an additional 3 hours, then cooled with ice water and treated dropwise over a period of one hour with a solution of 21.8 g. of 1-methyl-10,11-dihydro-5H-dibenzo[a,d]cyclohepten-5-one (J. Med. Pharm. Chem. 4, 335–49, 1961) in 400 ml. of dry ether. Subsequently, the mixture is stirred at 45°C. under reflux conditions for an additional 10 hours, then cooled with ice water and decomposed with a cold saturated ammonium chloride solution. The organic layer is removed by separation. The aqueous phase is shaken twice with 100 ml. portions of ether and the combined ether extracts are dried over sodium sulfate and evaporated. The residual 1-methyl-10,11-dihydro-5-(3-dimethylaminopropyl)-5-hydroxy-5H-dibenzo[a,d]cycloheptene has a melting point of 154°–155°C. after recrystallization from high-boiling petroleum ether.

EXAMPLE 2

Preparation of
1-methyl-10,11-dihydro-5-(3-dimethylaminopropyl)-5H-dibenzo[a,d]cycloheptene 39.5 g. of 1-methyl-10,11-dihydro-5-(3-dimethylaminopropylidene)-5H-dibenzo[a,d]cycloheptene are dissolved in 400 ml. of glacial acetic and hydrogenated at room temperature and under normal pressure in the presence of 3 g. of platinum oxide. When the uptake of hydrogen ceases, the catalyst is removed by filtration. The filtrate is evaporated, and the residue distilled whereby 1-methyl-10,11-dihydro-5-(3-dimethylaminopropyl)-5H-dibenzo[a,d]cycloheptene goes over at 140°C. under 0.01 mmHg. The corresponding hydrochloride salt has a melting point of 181°–183°C. after recrystallization from ethanol-ether.

EXAMPLE 3

Preparation of
1-methyl-10,11-dihydro-5-(3-methylamino-propylidene)-5H-dibenzo[a,d]cycloheptene 9.1 g. of 1-methyl-10,11-dihydro-5-(3-methylaminopropyl)-5-hydroxy-5H-dibenzo[a,d]cycloheptene and 100 ml. of 3% ethanolic hydrochloric acid are heated on the steam bath under reflux conditions for 3 hours and subsequently evaporated to dryness. The residual 1-methyl-10,11-dihydro-5-(3-methylamino-propylidene)-5H-dibenzo[a,d]cycloheptene hydrochloride has a melting point of 210°–228°C. after recrystallization from ethanol-ether and comprises a mixture of the α- and β-isomers.

The 1-methyl-10,11-dihydro-5-(3-methylaminopropyl)-5-hydroxy-5H-dibenzo[a,d]cycloheptene employed as the starting compound can be prepared as follows.

A solution containing 15.5 g. of 1-methyl-10,11-dihydro-5-(3-dimethylaminopropyl)-5-hydroxy-5-H-dibenzo[a,d]cycloheptene in 180 ml. of dry benzene is added dropwise to a mixture of 16.4 g. of chloroformic acid ethyl ester and 50 ml. of dry benzene and thereafter boiled at reflux for 20 hours. After cooling, the reaction mixture is washed with three 100 ml. portions of hydrochloric acid, then with water, dried over sodium sulfate and evaporated. The 1-methyl-10,11-dihydro-5-(3-methyl-carbethoxyaminopropyl)-5-hydroxy-5H-dibenzo[a,d]cycloheptene obtained is recrystallized from high-boiling petroleum ether and has a melting point of 132°–134°C.

12.5 g. of 1-methyl-10,11-dihydro-5-(3-methylcarbethoxyaminopropyl)-5-hydroxy-5H-dibenzo[a,d]cycloheptene, 14 g. of potassium hydroxide and 120 ml. of n-butanol are boiled at reflux for 17 hours under nitrogen and with strong stirring. The butanol is removed by distillation under reduced pressure. The residue is taken up in ether and washed with water. 1-Methyl-10,11-dihydro-5-(3-methylaminopropyl)-5-hydroxy-5H-dibenzo[a,d]cycloheptene is obtained as a thick oil by evaporation of the ether.

EXAMPLE 4

Preparation of
1-methyl-10,11-dihydro-5-(3-methylaminopropyl)-5H-dibenzo[a,d]cycloheptene 12.2 g. of 1-methyl-10,11-dihydro-5-(3-dimethylaminopropyl)-5H-dibenzo[a,d]cycloheptene, dissolved in 180 ml. of dry benzene, are added dropwise to a mixture of 13.6 g. of ethyl chloroformate and 50 ml. of dry benzene. The mixture is boiled and stirred under reflux for 20 hours. After cooling, the benzene solution is washed with dilute hydrochloric acid and water and evaporated. The residual 1-methyl-10,11-dihydro-5-(3-methylcarbethoxyaminopropyl)-5H-dibenzo[a,d]cycloheptene distils at 180°C/0.01 mmHg. 10.6 g. of 1-methyl-10,11-dihydro-5-(3-methylcarbethoxyaminopropyl)-5H-dibenzo[a,d]cycloheptene, 12.6 g. of potassium hydroxide and 110 ml. of n-butanol are boiled at reflux for 20 hours under an atmosphere of nitrogen with strong stirring. The butanol is removed by distillation under reduced pressure. The residue is taken up in ether and the etheral solution shaken with dilute hydrochloric acid. By treatment of the aqueous acidic phase with excess potassium carbonate, 1-methyl-10,11-dihydro-5-(3-methylaminopropyl)-5H-dibenzo[a,d]cycloheptene separates out as an oil which distils at 150°C. under 0.01 mmHg. After recrystallization from ethanol-ether, the hydrochloride has a melting point of 173°–175°C.

EXAMPLE 5

Preparation of
1-methyl-5-(3-dimethylaminopropylidene)-5H-dibenzo[a,d]cycloheptene 10 g. of 1-methyl-5-(3-dimethylaminopropyl)-5-hydroxy-5H-dibenzo[a,d]cycloheptene and 100 ml. of 3% ethanolic hydrochloric acid are heated under reflux conditions for 3 hours and subsequently evaporated to dryness. The residual 1-methyl-5-(3-dimethylaminopropylidene)-5H-dibenzo[a,d]cycloheptene hydrochloride has a melting point of 185°–195°C. after recrystallization from ethanol-ether and comprises a mixture of the α- and β-isomers. The free base boils at 158°C. under 0.01 mmHg.

The 1-methyl-5-(3-dimethylaminopropyl)-5-hydroxy-5H-dibenzo[a,d]cycloheptene employed as the starting compound can be prepared as follows.

22.2 g. of 1-methyl-10,11-dihydro-5H-dibenzo[a,d]cyclohepten-5-one are dissolved in 200 ml. of carbon tetrachloride, treated with 17.8 g. of bromosuccinimide and boiled at reflux for 2 hours. After cooling, the solution is filtered to remove the succinimide formed and evaporated. There remain 36.7 g. of a thick oil which is dissolved in 100 ml. of ethanol, treated with a solution containing 20 g. of potassium carbonate in 30 ml. of water and heated at reflux for 2 hours. The clear solution is evaporated to dryness, and the residue is dissolved in 200 ml. of methylene chloride. The methylene chloride solution is washed with water, dried over sodium sulfate and evaporated. The residual 1-methyl-5H-dibenzo[a,d]cyclohepten-5-one has a melting point of 84°–85°C. after recrystallization from ethanol.

20 g. of Gilman alloy are covered with 40 ml. of dry ether and treated with 0.5 ml. of methyl iodide. After the vigorous reaction has subsided somewhat, a solution containing 80 ml. of 1chloro-3-dimethylaminopropane in 360 ml. of dry ether is added dropwise in such a way that the reaction mixture is maintained at boiling. The mixture is stirred at 45°C. under reflux conditions for an additional 5 hours. The reaction mixture is then cooled with ice-water and a solution containing 43.6 g. of 1-methyl-5H-dibenzo[a,d]cyclohepten-5-one in 820 ml. of dry ether is added over a one-hour period. Subsequently, the mixture is boiled and stirred at reflux for another 17 hours. After about 12 hours, it is once more cooled with ice water and decomposed with a cold saturated ammonium chloride solution. The organic layer is separated, washed with water, dried over sodium sulfate and evaporated. The 1-methyl-5-(3-dimethylaminopropyl)-5-hydroxy-5H-dibenzo[a,d]cycloheptene obtained is recrystallized from high-boiling petroleum ether and has a melting point of 141°–143°C.

EXAMPLE 6

Preparation of
1-methyl-5-(3-methylaminopropylidene)-5H-dibenzo[a,d]cycloheptene 6.2 g. of 1-methyl-5-(3-methylaminopropyl)-5-hydroxy-5H-dibenzo[a,d]cycloheptene and 60 ml. of 3% ethanolic hydrochloric acid are heated under reflux conditions for 3 hours and evaporated to dryness. The residual 1-methyl-5-(3-methylaminopropylidene)-5H-dibenzo[a,d]cycloheptene hydrochloride, after recrystallization from ethanol-ether, has a melting point of 170°–180°C. and comprises a mixture of the α- and β-isomers. The free base boils at 150°C. under 0.01 mmHg.

The 1-methyl-5-(3-methylaminopropyl)-5-hydroxy-5H-dibenzo[a,d]cycloheptene employed as the starting compound can be prepared as follows.

A solution containing 30 g. of 1-methyl-5-(3-dimethylaminopropyl)-5-hydroxy-5H-dibenzo[a,d]cycloheptene in 100 ml. of dry benzene is added dropwise with stirring at 20°C. to a mixture of 31.8 g. of ethyl chloroformate in 100 ml. of dry benzene. Subsequently, the mixture is vigorously boiled under reflux conditions for 20 hours. After cooling, the benzene solution is washed with water, dilute hydrochloric acid and once again with water, dried over sodium sulfate and evaporated. The 1-methyl-5-(3-methylcarbethoxyaminopropyl)-5-hydroxy-5H-dibenzo[a,d]cycloheptene obtained has a melting point of 157°–159°C. after recrystallization from ethanol.

13.5 g. of 1-methyl-5-(3-methylcarbethoxyaminopropyl)-5-hydroxy-5H-dibenzo[a,d]cycloheptene, 120 ml. of n-butanol and 14.5 g. of potassium hydroxide are boiled at reflux under an atmosphere of nitrogen for 20 hours. The solution is then evaporated to dryness and the residue taken up in ether. The ethereal solution is shaken out with dilute hydrochloric acid. The aqueous, acidic solution is again made alkaline with potassium carbonate. The oil which separates out is extracted with ether. The ethereal solution is washed with water, dried over sodium sulfate and evaporated. The 1-methyl-5-(3-methylaminopropyl)-5-hydroxy-5H-dibenzo[a,d]cycloheptene obtained is a thick oil which is immediately utilized as a reactant.

EXAMPLE 7

Preparation of
1-methyl-5-(3-dimethylaminopropylidene)-5-H-dibenzo[a,d]cycloheptene N-oxide 1.9 g. of 1-methyl-5-(3-dimethylaminopropylidene)-5H-dibenzo[a,d]cycloheptene (a 1:1 isomeric mixture) are dissolved in 20 ml. of methanol at 0°C. and treated with 2.25 g. of 30% aqueous hydrogen peroxide solution. Subsequently, the mixture is stirred at 50°C. for an additional 16 hours. The excess hydrogen peroxide is decomposed by the addition of platinum black. After filtration, the solution is adjusted to pH 2 with methanolic hydrochloric acid and dried for 30 minutes at 20°C. under strongly reduced pressure. The residue is crystallized from methanol-ether, whereby 1-methyl-5-(3-dimethylaminopropylidene)-5H-dibenzo[a,d]cycloheptene N-oxide hydrochloride having a melting point of 179°–180°C. is obtained.

EXAMPLE 8

Preparation of
1-methyl-5-(3-dimethylaminopropylidene)-5H-dibenzo[a,d]cycloheptene A mixture containing 2 g. of 1-methyl-5-(3-chloropropylidene)-5H-dibenzo[a,d]cycloheptene (α- and β-isomers), 20 ml. of dry xylene and 5 g. of dimethylamine are heated for 15 hours at 100°C. in a pressure vessel. After cooling, the excess amine is evaporated under reduced pressure. The residue is taken up with ether, and the ethereal solution is shaken out with dilute hydrochloric acid. Then, the aqueous phase is separated and made alkaline with an excess of potassium carbonate. The precipitated oil is extracted with ether. The ethereal solution is washed with water, dried and evaporated whereby 1-methyl-5-(3-dimethylaminopropylidene)-5H-dibenzo[a,d]cycloheptene remains behind as a thick oil. The corresponding hydrochloride salt, after recrystallization from ethanol/ether, has a melting point of 188°–192°C. and comprises a mixture of α- and β-isomers.

The 1-methyl-5-(3-chloropropylidene)-5H-dibenzo[a,d]cycloheptene employed as the starting compound can be prepared as follows.

5 g. of magnesium chips are covered with 20 ml. of dry ether and treated with three drops of methyl iodide. When the vigorous reaction subsides somewhat, a solution containing 20 g. of 1-chloro-3-methoxy-propane in 100 ml. of dry ether is added dropwise in such a manner that the reaction mixture is maintained at boiling. Subsequently, the mixture is heated for an additional 3 hours at 45°C. under reflux conditions. Then, it is cooled with ice water, treated dropwise with a solution containing 17.7 g. of 1-methyl-5H-dibenzo[a,d]cyclohepten-5-one in 100 ml. of dry ether over a 1-hour period and again heated for 16 hours under reflux conditions at 45°C. Thereafter, the reaction mixture is cooled with ice water and treated with a cooled saturated ammonium chloride solution. The organic layer is separated, and the aqueous phase is shaken out with two 100 ml. portions of ether. The combined ether fractions are dried over sodium sulfate and evaporated. The residual 1-methyl-5-(3-methoxypropyl)-5-hydroxyl-5H-dibenzo[a,d]cycloheptene, after recrystallization from high-boiling petroleum ether, has a melting point of 112°–113°C.

22 g. of 1-methyl-5-(3-methoxypropyl)-5-hydroxy-5H-dibenzo [a,d]cycloheptene and 200 ml. of a 3% ethanolic hydrochloric acid solution are heated under reflux conditions for 3 hours. The residue, after removal of the ethanol, is taken up in ether. The ethereal solution is washed with water, sodium bicarbonate solution and again with water, dried over sodium sulfate and evaporated. The residual 1-methyl-5-(3-methoxypropylidene)-5H-dibenzo[a,d]cycloheptene boils at 150°C/0.01 mmHg and comprises a mixture of α- and β-isomers.

16.5 g. of 1-methyl-5-(3-methoxypropylidene)-5H-dibenzo [a,d]cycloheptene are dissolved in 60 ml. of methylene chloride, cooled to −10°C. and treated dropwise with a solution containing 7.7 g. of boron trichloride in 20 ml. of methylene chloride. After standing for 10 hours at room temperature, the reaction mixture is washed with water, a sodium bicarbonate solution and again with water, dried and evaporated. The residual 1-methyl-5-(3-chloropropylidene)-5H-dibenzo[a,d]cycloheptene has a boiling point of 145°C/0.01 mmHg.

EXAMPLE 9

Preparation of
1-methyl-5-(3-dimethylaminopropylidene)-5H-dibenzo[a,d]cycloheptene 5 g. of 1-methyl-5-(3-aminopropylidene)-5H-dibenzo[a,d]cycloheptene, 5 g. of 90% formic acid and 2.5 g. of paraformaldehyde are heated for 20 minutes under reflux conditions. After cooling, the reaction mixture is treated with a solution containing 4.5 g. of sodium hydroxide in 50 ml. of water. The precipitated oil is extracted with ether. The ethereal solution is washed with water, dried over sodium sulfate and evaporated. The residual 1-methyl-5-(3-dimethylaminopropylidene)-5H-dibenzo[a,d]cycloheptene distils at 155°–160°C. at 0.01 mmHg. The corresponding hydrochloride, after recrystallization from ethanol/ether, has a melting point of 186°–192°C. and comprises a mixture of α- and β-isomers.

The 1-methyl-5-(3-aminopropylidene)-5H-dibenzo[a,d]cycloheptene employed as the starting compound can be prepared as follows.

A mixture containing 10.1 g. of 1-methyl-5-(3-chloropropylidene)-5H-dibenzo[a,d]cycloheptene, 6.6 g. of potassium phthalimide and 20 ml. of nitrobenzene are heated together, with stirring, for 6 hours at 200°C. under reflux conditions. Then, the nitrobenzene is removed with water vapor, and the residue is taken up in methylene chloride. The methylene chloride solution is washed with water, dried and evaporated. The resulting 1-methyl-5-(3-phthalimidopropylidene)-5H-dibenzo[a,d]cycloheptene, after recrystallization from ethyl acetate/petroleum ether, has a melting point of 143°–169°C. and comprises a mixture of α- and β-isomers.

9.2 g. of 1-methyl-5-(3-phthalimidopropylidene)-5H-dibenzo [a,d]cycloheptene are dissolved in 100 ml. of ethanol, treated with 1.2 g. of hydrazine hydrate and heated for 6 hours under reflux conditions. An excess of concentrated hydrochloric acid is added, and the mixture is heated for an additional hour under reflux conditions. The reaction mixture is filtered warm. The solid residue is washed with warm ethanol, and the residual ethanol portions are evaporated to dryness. The residue is taken up in ether. The ethereal solution is washed with dilute sodium hydroxide solution, dried and evaporated whereby 1-methyl-5-(3-aminopropylidene)-5H-dibenzo[a,d]cycloheptene remains behind as a thick oil.

EXAMPLE 10

Preparation of 1-methyl-10,11-dihydro-5-(3-methylaminopropylidene)-5H-dibenzo[a,d]cycloheptene-p-toluenesulfonate 18 g. of 1-methyl-10,11-dihydro-5-(3-benzylideneaminopropyl)-5-hydroxy-5H-dibenzo[a,d]cycloheptene and 13.55 g. of toluenesulfonic acid methyl ester are mixed togehter and on an oil bath first heated slowly at 80° and thereafter at 130°C. The formed intermediate N-benzylidene-N-methyl-N-[3-(1-methyl-10,11-dihydro-5-hydroxy-5H-dibenzo[a,d]cyclohepten-5-yl)-propyl]ammonium-p-toluenesulfonate, then is converted directly to the 1-methyl-10,11-dihydro-5-(3-methylaminopropylidene)-5H-dibenzo [a,d]cycloheptene p-toluenesulfonate. After cooling, the mass is recrystallized from ethanol/ether. The resulting 1-methyl-10,11-dihydro-5-(3-methylaminopropylidene)-5H-dibenzo[a,d]cycloheptene-p-toluenesulfonate has a melting point of 175°–185°C. and comprises a mixture of α- and β-isomers. By known methods, it can be converted into other salts.

The 1-methyl-10,11-dihydro-5-(3-benzylideneaminopropyl)-5-hydroxy-5H-dibenzo[a,d]cycloheptene, employed as the starting compound, can be prepared as follows.

To a 250 ml. 3-neck vessel, equipped with a stirrer, a dropping funnel and an ammonia coolant, are added 75 ml. of liquid ammonia, and it is treated by adding a sodium chip to obtain a stable blue color. A solution containing 22.2 g. of 1-methyl-10,11-dihydro-5H-dibenzo[a,d]cyclohepten-5-one in 50 ml. of dry toluene is added dropwise with stirring. Thereafter, 4.6 g. of sodium are added piece by piece over a 30-minute period. The mixture is stirred for an additional 30 minutes and a solution containing 11.4 g. of freshly distilled 1-chloro-3-aminopropane in 40 ml. of dry toluene is added. The ammonia coolant is replaced by a water-cooler and the mixture is stirred overnight. The following morning, the mixture is cautiously decomposed with 50 ml. of water, whereby the 1-methyl-10,11-dihydro-5-(3-aminopropyl)-5-hydroxy-5H-dibenzo[a,d]cycloheptene partially crystallizes. Its melting point, after recrystallization from benzene/petroleum ether, is 155°–156°C. The crystals are removed by filtration and together with the separated toluene layer are treated with 13 g. of freshly distilled benzaldehyde. The mixture is heated at 80°C. under reduced pressure, so that the toluene and the residual water distil over. After recrystallization of the residue from ethanol, there is obtained 1-methyl-10,11-dihydro-5-(3-benzylideneaminopropyl)-5-hydroxy-5H-dibenzo [a,d]cycloheptene as colorless crystals having a melting point of 130°–131°C.

EXAMPLE 11

Preparation of 1-methyl-10,11-dihydro-5-(3-methylaminopropylidene)-5H-dibenzo[a,d]cycloheptene A Grignard compound prepared from 0.8 g. of magnesium, 5 g. of bromobenzene and 50 ml. of dry ether is treated with 8.7 g. of 1-methyl-10,11-dihydro-5-(propylidene)-5H-dibenzo[a,d]cycloheptene. The mixture is introduced to a vapor-free autoclave. The ether is removed through evacuation and light warming. Subsequently, the reaction mixture is cooled and after the introduction of 20 ml. of water-free methylamine is heated over a 65-hour period at 110°C. Thereafter, the reaction mixture is cooled and is taken up in ether. The excess methylamine is removed by distillation. The ethereal solution is washed with water and then shaken with dilute hydrochloric acid. The aqueous phase is separated and made alkaline with solid potassium carbonate. The oil which separates out is extracted with ether. The ethereal solution is washed with water, dried over sodium sulfate and evaporated. The resulting 1-methyl-10,11-dihydro-5-(3-methylaminopropylidene)-5H-dibenzo[a,d]cycloheptene is isolated as the hydrochloride and after recrystallization from ethanol/ether, has a melting point of 212°–226°C. and comprises a mixture of α- and β-isomers.

The 1-methyl-10,11-dihydro-5-(propylidene)-5H-dibenzo[a,d] cycloheptene employed as the starting compound can be prepared as follows.

5.25 g. of magnesium chips are treated with 7.6 g. of allyl bromide in 35 ml. of absolute ether. To the resulting allylmagnesium bromide solution, are added dropwise over a 1-hour period 14.6 g. of 1-methyl-10,11-dihydro-5H-dibenzo[a,d]cyclohepten-5-one in 50 ml. of ether and 50 ml. of benzene. Subsequently, the reaction mixture is heated under reflux conditions for 1 hour and then treated with a cold saturated ammonium chloride solution. The organic portion is separated. The aqueous phase is extracted with ether and the excess ethereal extract is evaporated. The yellow residual 1-methyl-10,11-dihydro-5-allyl-5-hydroxy-5H-dibenzo[a,d]cycloheptene is heated with 4 g. of acetic anhydride and 10 ml. of dry benzene with stirring at 90°C., treated with 0.3 ml. of acetylchloride and then for a short period heated at 110°C. The reaction mixture is cooled, diluted with ether and washed with aqueous ammonia until alkaline and dried. After evaporation of the ether, the residual product is 1-methyl-10,11-dihydro-5-(propylidene)-5H-dibenzo[a,d]cycloheptene is obtained as a yellow thick oil.

EXAMPLE 12

Preparation of
1-methyl-5-(3-methylcarbethoxyaminopropylidene)-5H-dibenzo[a,d]cycloheptene 6.9 g. of 1-methyl-5-(3-benzylmethylaminopropylidene)-5H-dibenzo[a,d]cycloheptene were dissolved in 15 ml. of dry benzene and treated once with 2.2 g. of ethyl chloroformate. Spontaneously, the reaction temperature does not go above 60°C. After remaining overnight at 20°C., the reaction mixture is diluted with benzene, washed with water, dilute hydrochloric acid, once again with water, dried and evaporated. The 1-methyl-5-(3-methylcarbethoxyaminopropylidene)-5H-dibenzo[a,d]cycloheptene remains behind as a thick yellow oil.

6.9 g. of 1-methyl-5-(3-methylcarbethoxyaminopropylidene)-5H-dibenzo[a,d]cycloheptene, 30 ml. of n-butanol and 6.7 g. of potassium hydroxide are heated togeter under an atmosphere of nitrogen, with vigorous stirring for 15 hours under reflux conditions. The n-butanol is distilled at reduced pressure, and the residue is taken up in ether. The ethereal solution is shaken with dilute hydrochloric acid. By treating the aqueous acidic phase with super-saturated potassium carbonate solution, there precipitates the 1-methyl-5-(3-methylaminopropylidene)-5H-dibenzo[a,d]cycloheptene as an oil, which distills at 150°C./0.01 mmHg. The corresponding hydrochloride, after recrystallization from ethanol/ether, has a melting point of 170°–180°C. and comprises a mixture of α- and β-isomers.

The 1-methyl-5-(3-benzylmethylaminopropylidene)-5H-dibenzo[a,d]cycloheptene, employed as the starting compound, can be prepared as follows.

7.1 g. of 1-methyl-5-(3-chloropropylidene)-5H-dibenzo[a,d] cycloheptene, 50 ml. of dry xylene and 10 g. of methylbenzylamine are heated together for 16 hours under reflux conditions. After cooling, the reaction mixture is diluted with ether, washed with water and shaken with dilute hydrochloric acid. The aqueous acidic solution is made alkaline with potassium carbonate. The precipitated oil is shaken with ether. After evaporation, the residual oily 1-methyl-5-(3-benzylmethylaminopropylidene)-5H-dibenzo[a,d]cycloheptene boils at 185°C./0.01 mmHg.

EXAMPLE 13

Preparation of
1-methyl-10,11-dihydro-5-(3-dimethylaminopropyl)-5H-dibenzo[a,d]cycloheptene 1.4 g. of Gilman alloy are covered with 10 ml. of dry ether and treated with three drops of methyl iodide. After the vigorous reaction subdues somewhat, there is added 5.5. ml. of 1-chloro-3-dimethylaminopropane in 25 ml. of dry ether and the reaction mixture is maintained at boiling. After the reaction mixture is heated at 45°C. under reflux conditions for 3 hours, it is cooled with ice water and treated dropwise over a 1-hour period with a solution containing 3.3 g. of 1-methyl-10,11-dihydro-5-chloro-5H-dibenzo[a,d]cycloheptene in 40 ml. of dry ether and 25 ml. of dry benzene. Subsequently, the reaction mixture is stirred under reflux conditions at 45°C. for another half hour and then cooled with ice water and decomposed with a cold saturated ammonium chloride solution. The ethereal portion is separated and shaken with dilute hydrochloric acid. The aqueous acidic solution is made alkaline with potassium carbonate. The precipitated oil is shaken out with ether. The ethereal solution is washed with water, dried over sodium sulfate and evaporated. The resulting 1-methyl-10,11-dihydro-5-(3-dimethylaminopropyl)- 5H-dibenzo[a,d] cycloheptene is isolated as the hydrochloride, which after recrystallization from ethanol/ether has a melting point of 181°–183°C.

The 1-methyl-10,11-dihydro-5-chloro-5H-dibenzo[a,d]cycloheptene, employed as the starting compound, can be prepared as follows.

10.7 g. of 1-methyl-10,11-dihydro-5H-dibenzo[a,d-]cyclohepten-5-one are dissolved in 200 ml. of methanol and treated dropwise with a solution containing 4 g. of sodium borohydride with stirring and a piece of potassium hydroxide in 50 ml. of water. The mixture is heated under reflux conditions for 2 hours. Then, the methanol is removed by distillation under reduced pressure and the residue is recrystallized from high-boiling petroleum ether whereby 1-methyl-10,11-dihydro-5-hydroxy-5H-dibenzo[a,d]cycloheptene is obtained as a colorless crystal, having a melting point of 108°–109°C.

To a solution containing 7 g. of 1-methyl-10,11-dihydro-5-hydroxy-5H-dibenzo[a,d]cycloheptene in 150 ml. of dry benzene is introduced dry hydrochloric acid over a 30-minute period. The solution is dried for a short period over calcium chloride, filtered and evaporated. The residual 1-methyl-10,11-dihydro-5-chloro-5H-dibenzo[a,d]cycloheptene, after recrystallization from high-boiling petroleum ether, has a melting point of 128°–130°C.

EXAMPLE 14

Preparation of
1-methyl-10,11-dihydro-5-(3-dimethylaminopropyl)-5H-dibenzo[a,d]cycloheptene N-oxide 17.3 g. of 1-methyl-10,11-dihydro-5-(3-dimethylaminopropyl)-5H-dibenzo[a,d]cycloheptene are dissolved in 200 ml. of methanol under an atmosphere of argon, treated with 20 g. of 30% hydrogen peroxide solution and heated at 50°C. for 17 hours. After cooling to −10°C., the excess hydrogen peroxide is decomposed through the addition of 3.5 g. of platinum black. The entire mixture is filtered, acidified with methanolic hydrochloric acid and evaporated to dryness under reduced pressure. The residue is dissolved in 100 ml. of methanol, treated with 800 ml. of ether and cooled to −15°C. whereby 1-methyl-10,11-dihydro-5-(3-dimethylaminopropyl)-5H-dibenzo[a,d]cycloheptene N-oxide hydrochloride crystallizes out and has a melting point of 157.5°–160°C.

EXAMPLE 15

Preparation of
1-methyl-10,11-dihydro-5-(3-dimethylaminopropylidene)-5H-dibenzo[a,d]cycloheptene N-oxide In an analogous manner to the procedure of Example 14, there is obtained from 18.9 g. of 1-methyl-10,11-dihydro-5-(3-dimethylaminopropylidene)-5H-dibenzo[a,d]cycloheptene (a mixture of geometric isomers = 1:1), 200 ml. of methanol and 22 g. of 30% hydrogen peroxide, 1-methyl-10,11-dihydro-5-(3-dimethylaminopropylidene)-5H-dibenzo[a,d]cycloheptene N-oxide hydrochloride having a melting point of 173°–175°C.

EXAMPLE 16

Preparation of 1-acetyl-10,11-dihydro-5-(3-dimethylaminopropylidene)-5H-dibenzo[a,d]cycloheptene 7.8 g. of 1-(2-methyl-1,3-dioxolan-2-yl)-10,11-dihydro-5-(3-dimethylaminopropyl)-5-hydroxy-5H-dibenzo[a,d]cycloheptene are heated with 50 ml. of ethanol and 6 ml. of 25% ethanolic hydrochloric acid over a 2½ hour period at reflux. Thereafter, the reaction mixture is concentrated under vacuum, dissolved in water, made alkaline with dilute sodium hydroxide and extracted with ether. The extract is washed with water, dried with sodium sulfate, filtered and evaporated whereby there is obtained 1-acetyl-10,11-dihydro-5-(3-dimethylaminopropylidene)-5H-dibenzo[a,d]cycloheptene as a yellow oil, whose NMR and IR spectrum are in agreement with their constitution. Through mass chromatography, it is determined that the product is a mixture of the geometric isomers α (30%) and β (70%).

The 1-(2-methyl-1,3-dioxolan-2-yl)-10,11-dihydro-5-(3-dimethylaminopropyl)-5-hydroxy-5H-dibenzo[a,d]cycloheptene, employed as the starting compound, can be prepared as follows.

4.8 g. of Gilman alloy are added to 20 ml. of absolute tetrahydrofuran and a solution containing 25 g. of O-cyanobenzylchloride in 125 ml. of absolute tetrahydrofuran is added thereto. Subsequently, the reaction mixture is heated for 2 hours at reflux and an additional 25 g. of O-cyanobenzylchloride and 125 ml. of tetrahydrofuran are added dropwise. Thereafter, the mixture is heated for an additional 18 hours at reflux. Subsequently, there is added 60 ml. of saturated ammonium chloride solution and some diluted hydrochloric acid whereupon the reaction mixture is extracted with ether. Theh ethereal solution is washed with water, dried and evaporated, whereby there is obtained α,α'-bis-o-toluenenitrile which after recrystallization from 200 ml. of ethanol, has a melting point of 135°–139°C.

60 g. of α,α'-bis-o-toluenenitrile are heated at reflux under an atmosphere of argon with 58 g. of potassium hydroxide, 50 g. of water and 180 ml. of ethylene glycol over a 96-hour period. After cooling, the mixture is filtered and washed with ethyl acetate. Subsequently, the alkaline solution is acidified and extracted with methylene chloride. The extract is washed with water, dried and evaporated. The residue is recrystallized from absolute ethanol, whereby α,α'-bis-o-toluic acid is obtained having a melting point of 234°–236°C.

54 g. of α,α'-bis-o-toluic acid are treated with 215 g. of polyphosphoric acid at 160°C. and stirred for 2 hours. After cooling, the reaction mixture is separated between water and ether. The ethereal phase is extracted with sodium hydroxide solution. From the aqueous phase, through acidification, there is obtained 1-carboxy-10,11-dihydro-5H-dibenzo[a,d]cyclohepten-5-one, which after recrystallization from ethanol/water, has a melting point of 188°–189°C.

25 g. of 1-carboxy-10,11-dihydro-5H-dibenzo[a,d]cyclohepten-5-one in 250 ml. of benzene are heated with 20 g. of oxalyl chloride for 2 hours at reflux and subsequently concentrated under reduced pressure. The resulting crystalline 1-chlorocarbonyl-10,11-dihydro-5H-dibenzo[a,d]cyclohepten-5-one is dissolved in 200 ml. of benzene and then it is added dropwise to a solution of the magnesium salt of diethyl malonate (about 50 g. in 500 ml. of ether) over a period of about 5 minutes and heated at reflux for 12 hours. Subsequently, the reaction mixture is divided between ether and dilute sulfuric acid, washed with water, sodium bicarbonate solution and water, dried and evaporated. The residue is heated in 30 ml. of ethyl acetate, 20 ml. of water and 3.7 ml. of concentrated sulfuric acid at reflux for 15 hours. Then, it is poured over ice water and extracted with ether. The ethereal extract is washed with water, sodium bicarbonate solution and water, dried and evaporated, whereby 1-acetyl-10,11-dihydro-5H-dibenzo[a,d]cyclohepten-5-one having a melting point of 65°–68°C. is obtained.

7.4 g. of 1-acetyl-10,11-dihydro-5H-dibenzo[a,d]cyclohepten-5-one, 9.5 g. of ethylene glycol, 30 ml. of toluene and 60 mg. of p-toluenesulfonic acid are heated in a water separator at reflux for 8 hours. Thereafter, the mixture is concentrated under reduced pressure, taken up in ethyl acetate, washed with sodium carbonate solution and water, dried and evaporated, whereby 1-(2-methyl-1,3-dioxolan-2-yl)-10,11-dihydro-5H-dibenzo[a,d]cyclohepten-5-one is obtained as yellow crystals having a melting point of 144°–145°C. (from ethyl acetate/petroleum ether).

Utilizing 1.13 g. of Gilman alloy, 5 ml. of absolute ether, 5.2 g. of dimethylaminoproyl chloride and 5 ml. of absolute tetrahydrofuran, in a similar manner, is obtained the corresponding Grignard compound. After cooling to 0°C., there is added dropwise a solution containing 7.2 g. of 1-(2-methyl-1,3-dioxolan-2-yl)-10,11-dihydro-5H-dibenzo[a,d]cyclohepten-5-one in 40 ml. of absolute tetrahydrofuran. Subsequently, the mixture is heated for 3 hours at reflux, cooled to about 0°C., hydrolyzed with 4 ml. of water, filtered, and then washed with ether. The ethereal solution is dried over sodium sulfate, filtered and concentrated under reduced pressure, whereby 1-(2-methyl-1,3-dioxolan-2-yl)-10,11-dihydro-5-(3-dimethylaminopropyl)-5-hydroxy-5H-dibenzo[a,d]cycloheptene is obtained as a yellow oil which is crystallized from 50 ml. of high-boiling petroleum ether and has a melting point of 122°–124°C.

EXAMPLE 17

Preparation of 1-methyl-5-(3-dimethylaminopropyl)-5H-dibenzo[a,d]cycloheptene A Grignard reagent is prepared in usual manner from 7 g. of Gilman alloy in 20 ml. of absolute ether and 33.6 g. of 3-dimethylaminopropylchloride in 50 ml. of absolute tetrahydrofuran. The solvent is distilled off in an argon atmosphere and replaced by 150 ml. of absolute benzene. A solution of 20 g. of 5-chloro-1-methyl-5H-dibenzo[a,d]cycloheptene in 250 ml. of absolute benzene is added dropwise at room temperature. The mixture is heated for 15 minutes under reflux condition, is hydrolyzed with 50 ml. of water, filtered, washed three times with chloroform and evaporated under reduced pressure. After working up in usual manner, oily 1-methyl-5-(3-dimethylaminopropyl)-5H-dibenzo[a,d]cycloheptene (mixture of the diastereomers in the proportion of about 1:1) is obtained. The corresponding maleate is a cryatalline compound which melts at 130°–131°C. (mixture of the diastereomers in the proportion of about 2:1). The 5-chloro-1-methyl-5H-dibenzo[a,d] cycloheptene used above as starting material can be prepared as follows:

26 g. of 1-Methyl-5H-dibenzo[a,d]cyclohepten-5-one are dissolved in 200 ml. of dioxane, a solution of 9 g. of sodium borohydride in 35 ml. of water is added thereto and the mixture is stirred at room temperature for 4 hours. The mixture is subsequently evaporated under reduced pressure. The residue is shaken with ether and water. The ethereal phase is washed with water, dried over sodium sulfate, filtered and evaporated. The 5-hydroxy-1-methyl-5H-dibenzo[a,d]cycloheptene obtained is recrystallized from petroleum ether and melts at 114°–116°C.

23 g. of 5-Hydroxy-1-methyl-5H-dibenzo[a,d]cycloheptene in 200 ml. of absolute benzene are heated with 45 ml. of thionylchloride for two hours under reflux conditions. The mixture is subsequently evaporated under reduced pressure. The resulting, white crystalline residue is recrystallized from carbon tetrachloride. 5-Chloro-1-methyl-5H-dibenzo[a,d]cycloheptene, melting at 158°–160°C., is obtained.

EXAMPLE 18

Preparation of
1-methyl-5-(3-dimethylaminopropyl)-5H-dibenzo[a,d-]cycloheptene-N-oxide 10 g. of 1-Methyl-5-(3-dimethylaminopropyl)-5H-dibenzo[a,d]cycloheptene (mixture of the diastereomers in the proportion of about 1:1) are heated in 100 ml. of methanol with 7.8 g. of 30% aqueous hydrogen peroxide solution for 20 hours at 50°C. Working up is effected as in Example 14. 1-Methyl-5-(3-dimethyaminopropyl) 5H-dibenzo[a,d]cycloheptene-N-oxide is obtained, melting at 180°–181°C.

EXAMPLE 19

Preparation of tablets:

| | |
|---|---|
| 1-Methyl-10,11-dihydro-5-(3-methylaminopropyl)-5H-dibenzo[a,d]cycloheptene hydrochloride | 28.05 g. |
| Lactose | 110 g. |
| Corn Starch | 57.95 g. |
| Talc | 3.50 g. |
| Magnesium Stearate | 0.6 g. |
| | 200.00 g. |

The ingredients are intimately mixed with one another and pressed into 200 mg. tablets, which are subsequently coated with ethyl cellulose and Carbowax.

We claim:
1. A compound of the formula

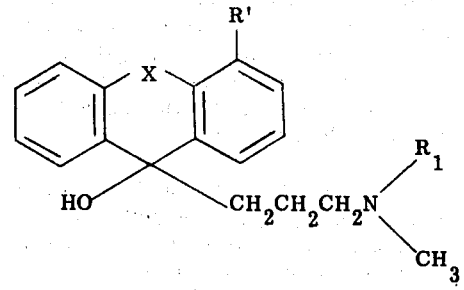

wherein $R_1$ is hydrogen or methyl; X is ethylene or vinylene, and R' is a ketalized acetyl group,
or its N-oxide when $R_1$ is methyl.

2. A compound in accordance with claim 1, wherein R' is 2-methyl-1,3-dioxolan-2-yl, $R_1$ is methyl and X is ethylene, i.e., 1-(2-methyl-1,3-dioxolan-2-yl)-10,11-dihydro-5-(3-dimethylaminopropyl)-5-hydroxy-5H-dibenzo[a,d]cycloheptene.

* * * * *